United States Patent [19]

Lagana et al.

[11] 4,252,771
[45] Feb. 24, 1981

[54] METHANATION REACTOR

[75] Inventors: Vincenzo Lagana, Milan; Francesco Saviano, Segrate; Stanislao Ferrantino, San Donato Milanese, all of Italy

[73] Assignee: Asnaprogetti S.p.A., Milan, Italy

[21] Appl. No.: 893,347

[22] Filed: Apr. 4, 1978

[30] Foreign Application Priority Data

Apr. 15, 1977 [IT] Italy .................................. 22499 A/77

[51] Int. Cl.³ .......................... F28D 21/08; B01J 8/02; C07C 29/16; F16J 15/14
[52] U.S. Cl. .............................. 422/198; 260/449 M; 422/208; 422/211; 422/240
[58] Field of Search ............... 422/148, 198, 208, 211, 422/218, 240, 242, 207, 220; 277/230, 3, 135; 260/449 M

[56] References Cited

U.S. PATENT DOCUMENTS

| | | | |
|---|---|---|---|
| 1,704,214 | 3/1929 | Richardson | 422/148 X |
| 2,051,774 | 8/1936 | Kleinschmidt | 422/208 |
| 2,109,118 | 2/1938 | Naumann | 422/240 X |
| 2,339,368 | 1/1944 | Bagsar | 422/240 X |
| 2,667,804 | 2/1954 | Boyer et al. | 277/230 X |
| 2,883,214 | 4/1959 | Perlaki | 277/3 |
| 3,041,150 | 6/1962 | Worn | 422/242 X |
| 3,284,163 | 11/1966 | Dear | 277/230 X |
| 3,440,021 | 4/1969 | Niedetzky et al. | 422/198 X |
| 3,477,828 | 11/1969 | Schulze et al. | 422/148 |
| 3,492,099 | 1/1970 | Sze | 422/148 |
| 3,516,800 | 6/1970 | Yamamoto et al. | 422/148 |
| 3,663,179 | 5/1972 | Mehta et al. | 422/148 |
| 3,994,503 | 11/1976 | Dousse et al. | 277/3 |

FOREIGN PATENT DOCUMENTS 892743  8/1953  Fed. Rep. of Germany .......... 422/207

Primary Examiner—Joseph Scovronek
Attorney, Agent, or Firm—Morgan, Finnegan, Pine, Foley & Lee

[57] ABSTRACT

A methanation reactor, to be used preferably in an integrated urea-ammonia process for methanizing carbon oxides is disclosed, in which the catalyst bed and an underlying heat exchanger of the tube-bundle type make up a unit mounted centrally of the reactor casing with a gap left between the reactor casing inside wall and said centrally mounted unit. Fresh gases to be methanized enter the gap, then the heat exchanger from below and flow upwards to the catalyst bed, whereafter they flow down to the exchanger again. Incoming gases sweep the exchanger tubes from the outside, while the reacted gases flow in the interior of the tubes of the heat exchanging bundle. Insulation blankets and gland seals are provided.

3 Claims, 3 Drawing Figures

METHANATION REACTOR

This invention relates to a methanation reactor. More particularly, the present invention relates to a methanation reactor which has, inserted therein, a heat exchanger for preheating the cold gases to be sent to the catalytic reaction.

Methanation reactors are known: they are vertical cylindrical holders which contain in their interior one or more layers of a catalyst. Their operation, summarized concisely, is as follow: the hot gases to be methanized enter the reactor at a temperature of about 300° C., flow through the catalyst bed, wherein they are reacted, and exit the reactor at a temperature of about 350° C. The hot gaseous mixture thus obtained is sent to an external heat exchanger so as to preheat to about 300° C. the cold gases to be sent to methanation.

The methanation reactor constructed according to the conventional technology has the disadvantage that it causes the hot gases to be reacted to contact the reactor casing for a certain time and this fact makes it compulsory to work under low pressures or to construct the reactor casing very expensive types of stainless steels, or to use refractory linings for shielding such casing from the direct contact with the gases. The latter approach involves a further increase in initial costs because, due to the considerable thickness of the linings, the size of the reactors must consequently be enlarged.

It has surprisingly been found, by virtue of the present invention, that the same results can be obtained, from the point of view of the methanized products, by using a reactor having a tubebundle heat exchanger inserted therein, which is positioned beneath the toroidal catalyst bed, and by adopting a circulation of cold gases to be reacted within the gap between the reactor casing and the catalyst bed-heat exchanger assembly.

By so doing, the inner walls of the casing and the casing as such are, during the reaction, at a comparatively low temperature and thus they can be constructed with a quite common carbon steel, or, at the most, with a steel having a low percentage of added alloying elements.

This fact permits the ammonia synthesis gases to be methanized with yields which are equal to those of the methods known heretofore, with the undeniable advantage that it becomes possible to use, for the reactor casing, which is subjected to the action of comparatively high pressures, a less sophisticated and thus less expensive material. Especially advantageous, in this respect, are the carbon steels and the steels containing a low percentage of alloying elements, up to 0.5% of molybdenum.

An object of the present invention is to provide a methanation reactor in which the cold gases to reacted enter through the top of the reactor, flow in the gap between the reactor casing and the catalyst bed-heat exchanger assembly, wherein they undergo a slight heating since they must keep the casing cold, rise through the central portion of the reactor and sweep the tubes of the exchanger, (through which the reacted hot gases flow), and are heated until attaining the temperature which is suitable for the reaction. At this stage the preheated gases to be reacted rise through a tube which is coaxial with the catalyst bed and then flow downwardly through the catalyst, wherein they react and are sent into the tubes of the exchanger so as to transfer their reaction heat to the incoming cold gases through the exchanger tube walls. At this stage, the outcoming cooled reactor gases emerge through the reactor bottom wall and are ready for possible subsequent operations.

Figure 1:
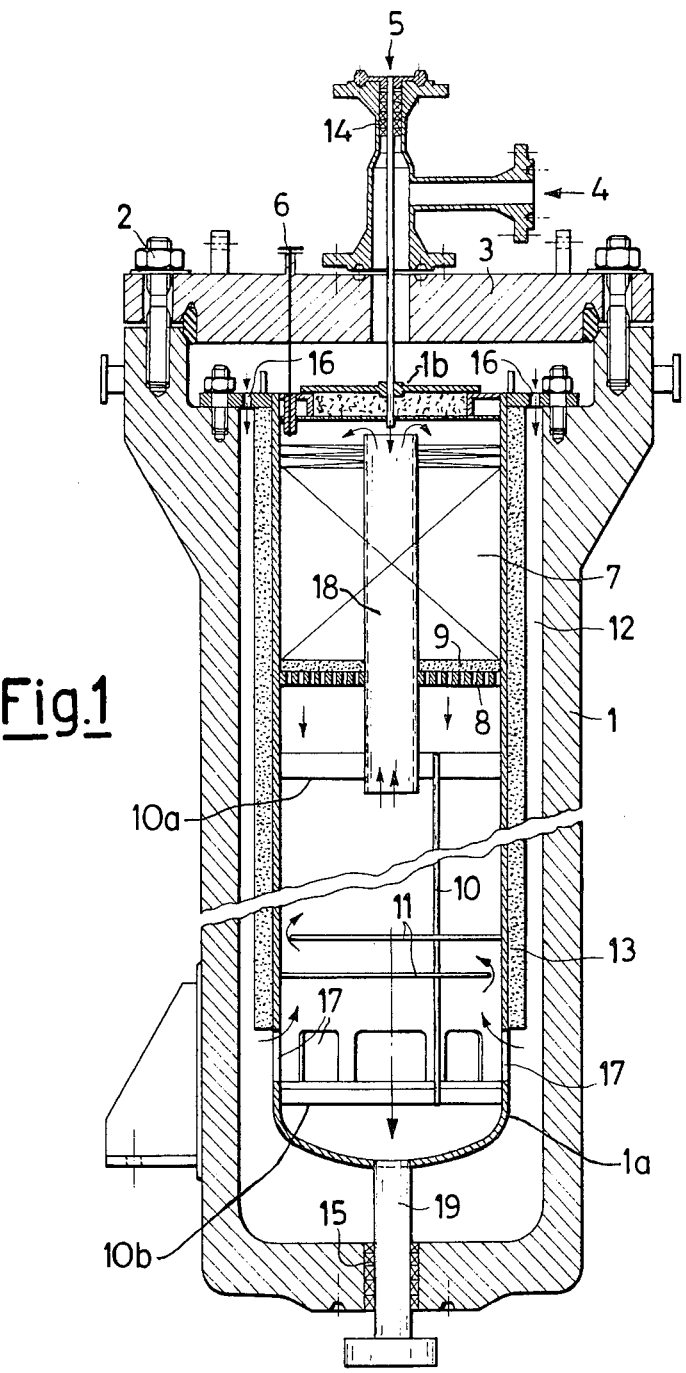
FIG. 1 is a longitudinal cross-sectional view of the reactor.

With reference to the diagram of FIG. 1, which is a longitudinal cross-sectional view of the reactor, and which does not limit the present invention, the operation of the methanation reactor will now be described in more detail.

The reactor is composed of an outer casing 1 to which the lid 3 is affixed by a set of bolts 2. To the lid 3, in turn, are fastened the tube 4 for introducing the fresh mixture of gases to be reacted during the normal operation run, the tube 5 for introducing the hot gases for starting the reactor operation and the operability of which will be described later, and a well 6, for introducing the thermocouples.

In the interior of the outer casing 1 is mounted an inner casing 1a having cover means 1b and in which a toroidal catalyst bed is positioned, indicated at 7, and is supported by a grid 8 and a layer of alumina balls 9, and, beneath the catalyst bed, the tube bundle heat exchanger 10, of which a single tube only is shown in order not to overcrowd the drawing, is installed: the exchanger is fitted with deflecting baffles 11, in order to improve the heat transfer from the hot gases to the cold ones. As illustrated, the single tube shown, of which a plurality thereof will make up the heat exchanger 10, is provided with transversely extending top and bottom tube sheet plates 10a and 10b respectively, which function to retain the individual tubes of the heat exchanger in place. A central pipe 18 has its lower end extending centrally through the upper sheet plate 10a of the heat exchanger 10. The central pipe 18 extends upwardly and centrally through the support 8 and the catalyst bed 7, with the upper end of the tube extending upward beyond the top of the catalyst bed.

Between the reactor outer casing 1 and the inner casing 1a containing the catalyst bed and the heat exchanger, there is a gap 12. The inner casing is heat-insulated by a layer of insulating material 13, which can be composed by glass-wool, rock-wool or, also, asbestos powder. At the inlet and the outlet of the gases into and from the reactor, there are sennit seals, 14 and 15, to be described in more detail in connection with FIGS. 2 and 3, and the way of operation of which will also be explained hereinafter.

The cold gases enter the methanation reactor through the pipe 4, flow through the gap 12 and via the windows 17 positioned within the inner casing 1a having cover means 1b and adjacent the lower end thereof and just above the bottom tube sheet 10b, enter the heat exchanger 10 to become heated thereby. The heated gases rise upwardly through the central pipe 18 and then flow downwardly through the interior of the catalyst bed 7. The reacted gases exit from the catalyst bed and then flow downwardly through the exchanger tubes 10 (in their interior), are cooled thereby and exit the methanation reactor through the pipe 19.

Figure 2:
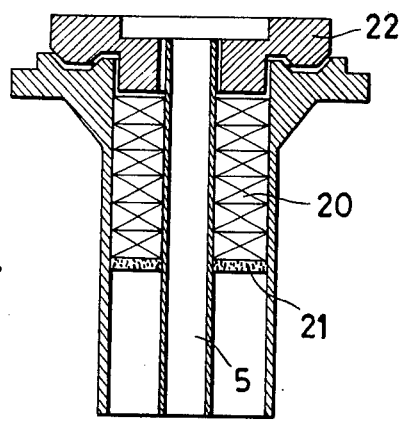
FIG. 2 is a diagrammatical showing of sennit seal system.

When the reactor is started, or restarted in the cold, it is necessary that a certain amount of hot gases to be reacted be fed, heated to the reaction temperature, and thus such gases can be introduced through the duct 4 to avoid heating the casing walls. To prevent this, the reacting hot gases are fed directly to the catalyst via the duct 5, whereas the cold gases are fed through the duct 4, as before. To prevent the admixture of the hot gases with the cold ones, the sennit seal system 14 has been adopted, which is best seen in FIG. 2. The seal system comprises the sennit braids 20, the abutments 21 and the packing gland 22 which urges the sennit against the abutments, so providing a tight seal for the cold gases. Another sealing problem is present at the bottom of the methanation reactor where, due to downward expansion of the duct 19, there can be leaks of reacting gases in the area of contact between the duct and the casing walls.

To solve this problem, a gland seal system is adopted which is equipped with an intermediate hollow bushing and permits the forced circulation of water under pressure to prevent dangerous processing gases from escaping the reactor.

Figure 3:
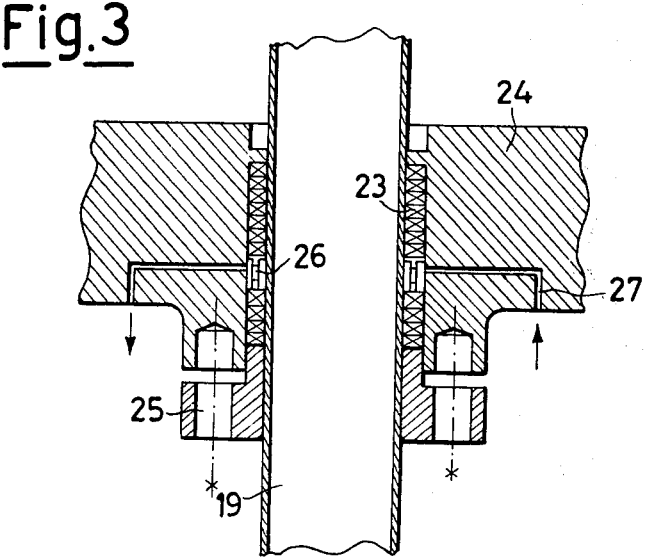
FIG. 3 is a diagrammatical showing of a gland seal system.

FIG. 3 is a diagrammatical showing of this particular kind of seal. Between the outside wall of the duct 19 and the casing 1 there is arranged an asbestos braid 23 (sennit) which is kept pressed in position by the reactor bottom wall 24 and by a flanged gland 25. The sennit is divided into two slugs by a bushing 26: the latter is connected via a channel 27 to a source of water under pressure. Whenever a leak occurs in the seal system, the reacting gases cannot exit the reactor since water enters the reactor under a pressure which exceeds the pressure existing in the reactor.

The kind of methanation reactor as described in the foregoing is particularly advantageous in the integrated ammonia-urea plants since it permits the methanation of $CO_2$ and CO under the same pressure existing in the ammonia reactor. Thus, the necessity of compressing the methanized gaseous mixture up to the pressure of the synthesis is eliminated, which is no little advantage.

We claim:

1. A methanation reactor comprising an outer metal casing having a removable lid mounted to the top portion of said casing, said lid having an aperture extending therethrough for introducing gases to be reacted into the outer casing, an inner casing having cover means and positioned within said outer casing in circumferentially spaced and supported relationship therefrom forming an axially extending vertical gap between said inner and outer casings for the downward vertical passage therethrough of gases to be reacted, a toroidal catalyst bed positioned in the upper portion of said inner casing, a transverse grid having a plurality of alumina balls located thereon positioned within said casing and supporting said catalyst bed, a heat exchanger assembly mounted within said inner casing below and in downwardly spaced relationship from said catalyst bed, said heat exchanger assembly including an upper horizontal tube sheet, a lower horizontal tube sheet and a plurality of vertical tubes connected at their respective upper and lower ends to said upper and lower tube sheets, said heat exchanger assembly also including a plurality of baffles to direct the upward flow of incoming gases within said heat exchanger assembly, said inner casing having a plurality of windows circumferentially spaced at the bottom end thereof below said heat exchanger assembly through which gases to be reacted will enter the inner casing from the lower end of the gap formed between the inner and outer casings, insulation means enveloping the outer surface of said inner casing from the top thereof down to the windows therein, a gas outlet tube centrally positioned within the upper portion of said inner casing, said outlet tube having its lower end mounted to the upper tube sheet of and extending into said heat exchanger assembly and its upper end extending through the beyond said catalyst bed, a central feed tube extending through the aperture in the lid of the outer casing and through the cover means of said inner casing and terminating at a point just above the upper end of the gas outlet tube for the passage of hot gases into the inner casing of said reactor, and gas discharge means centrally connecting at one end to the bottom of said inner casing and extending through the bottom end of said outer casing to provide an exit for reacted gases from the reactor, whereby the gases to be reached are fed initially through the aperture in the lid into the outer casing and thereafter downwardly through the gap between the inner and outer casings, then through the windows in the lower end of said inner casing and upwardly through the heat exchange assembly and about the tubes for preheating of the gas and thereafter collected in the upper end of the heat exchange assembly and fed upwardly through said gas outlet tube above the catalyst bed and then fed downwardly through the catalyst bed surrounding the gas outlet tube and then into and through the heat exchanger tubes and then downwardly through the gas discharge means in the bottom of the inner casing.

2. A methanation reactor in accordance with claim 1, wherein bushing means are provided for the gas discharge means between the gas discharge means and its engagement with the bottom end of the outer casing, and means for introducing water about the bushing under pressure to prevent the escape of gases.

3. A methanation reactor in accordance with claim 1, wherein thermocouple controls extend through the lid of the outer casing and the cover means of the inner casing to monitor the temperature of the gases.

* * * * *

UNITED STATES PATENT AND TRADEMARK OFFICE
CERTIFICATE OF CORRECTION

PATENT NO. : 4,252,771

DATED : February 24, 1981

INVENTOR(S) : Vincenzo Lagana, Francesco Saviano and Stanislao Ferrantino

It is certified that error appears in the above-identified patent and that said Letters Patent are hereby corrected as shown below:

Title page, item [73], change "Asnaprogetti" to read

--Snamprogetti--.

Signed and Sealed this

Nineteenth Day of May 1981

[SEAL]

Attest:

RENE D. TEGTMEYER

Attesting Officer

Acting Commissioner of Patents and Trademarks